US00PP35229P3

(12) United States Plant Patent
Post

(10) Patent No.: US PP35,229 P3
(45) Date of Patent: Jun. 20, 2023

(54) ***CHRYSANTHEMUM* PLANT NAMED 'DLFMARA1'**

(50) Latin Name: ***Chrysanthemum* X *morifolium***
Varietal Denomination: DLFMARA1

(71) Applicant: Arie Gerard Post, Delft (NL)

(72) Inventor: Arie Gerard Post, Delft (NL)

(73) Assignee: DELIFLOR ROYALTIES B.V., Maasdijk (NL)

( * ) Notice: Subject to any disclaimer, the term of this patent is extended or adjusted under 35 U.S.C. 154(b) by 0 days.

(21) Appl. No.: 17/967,300

(22) Filed: Oct. 17, 2022

(65) Prior Publication Data

US 2023/0132404 P1 Apr. 27, 2023

Related U.S. Application Data

(60) Provisional application No. 63/271,386, filed on Oct. 25, 2021.

(51) Int. Cl.
*A01H 5/02* (2018.01)
*A01H 6/14* (2018.01)

(52) U.S. Cl.
USPC ..... Plt./294

(58) Field of Classification Search
USPC ..... Plt./294, 288
CPC ... A01H 5/02; A01H 5/00; A01H 6/14; A01H 6/1424
See application file for complete search history.

(56) References Cited

PUBLICATIONS

CPVO Register Apr. 3, 2022 for *Chrysanthemum* DLFMARA1, retrieved on Dec. 12, 2022 at https://online.plantvarieties.eu/publicConsultationDetails?registerId=20213322&denomination=dlfmara1, 3 pp. (Year: 2022).*

* cited by examiner

*Primary Examiner* — June Hwu
(74) *Attorney, Agent, or Firm* — C. Anne Whealy

(57) ABSTRACT

A new and distinct cultivar of *Chrysanthemum* plant named 'DLFMARA1', characterized by its upright plant habit; uniform growth habit; vigorous growth habit and rapid growth rate; durable dark green-colored leaves; strong upright flowering stems; freely flowering habit; anemone-type inflorescences with white-colored ray florets; relative tolerance to low and high production temperatures; relative resistance to White Rust; and good postproduction longevity.

2 Drawing Sheets

Figure 1:
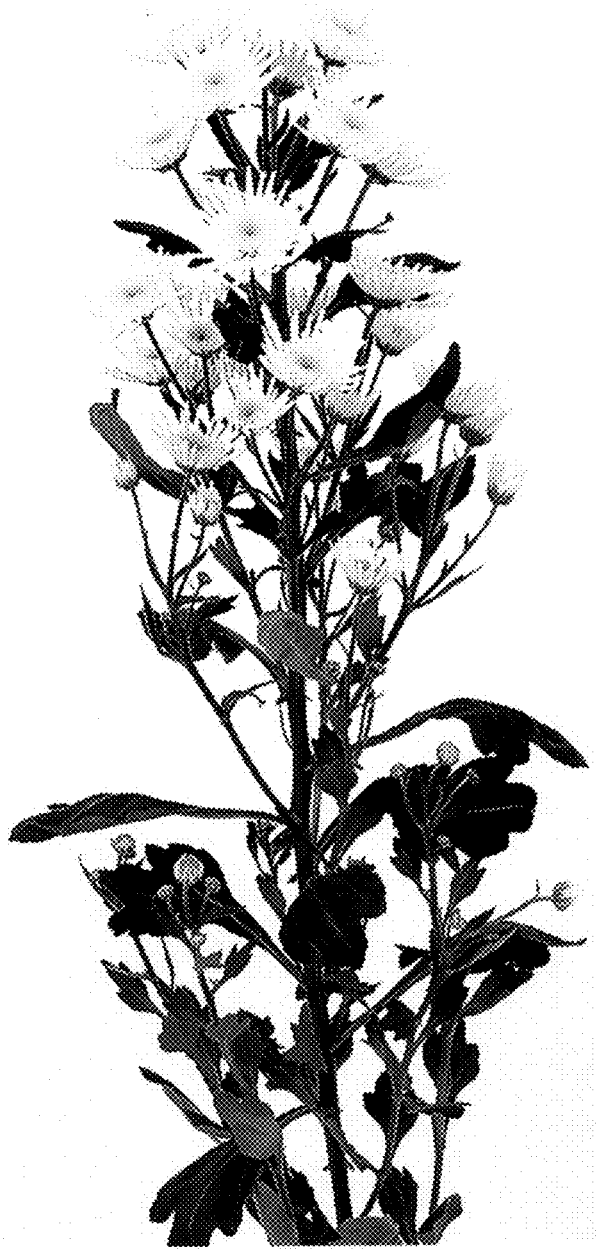

Botanical designation: *Chrysanthemum* X *morifolium*.
Cultivar denomination: 'DLFMARA1'.

A Japanese Plant Breeder's Rights application for the instant plant was filed by the Assignee, Deliflor Royalties B.V. of Maasdijk, The Netherlands on Jun. 21, 2021, application number 35513. Foreign priority is not claimed to this application.

BACKGROUND OF THE INVENTION

The present invention relates to a new and distinct cultivar of *Chrysanthemum* plant, botanically known as *Chrysanthemum* x *morifolium*, typically grown as a cut flower *Chrysanthemum* and hereinafter referred to by the name 'DLFMARA1'.

The new *Chrysanthemum* plant is a product of a planned breeding program conducted by the Inventor in Maasdijk, The Netherlands. The objective of the breeding program is to create new cut flower *Chrysanthemum* plants with unique and attractive inflorescences.

The new *Chrysanthemum* plant originated from a cross-pollination in February, 2018 of a proprietary selection of *Chrysanthemum* x *morifolium* identified as code number KR 2008.6601-1, not patented, as the female, or seed, parent with a proprietary selection of *Chrysanthemum* x *morifolium* identified as code number KR 2013.2342-1, not patented, as the male, or pollen, parent. The new *Chrysanthemum* plant was discovered and selected as a single flowering plant from within the progeny of the stated cross-pollination in a controlled greenhouse environment in Maasdijk, The Netherlands in April, 2019.

Asexual reproduction of the new *Chrysanthemum* plant by vegetative terminal cuttings in a controlled greenhouse environment in Maasdijk, The Netherlands since April, 2019 has shown that the unique features of this new *Chrysanthemum* plant are stable and reproduced true to type in successive generations of asexual reproduction.

SUMMARY OF THE INVENTION

The following traits have been repeatedly observed and are determined to be the unique characteristics of 'DLFMARA1'. These characteristics in combination distinguish 'DLFMARA1' as a new and distinct *Chrysanthemum* plant:

1. Upright plant habit; uniform growth habit.
2. Vigorous growth habit and rapid growth rate.
3. Durable dark green-colored leaves.
4. Strong upright flowering stems.
5. Freely flowering habit.
6. Anemone-type inflorescences with white-colored ray florets.
7. Relatively tolerant to low and high production temperatures.

8. Relatively resistant to White Rust.
9. Good postproduction longevity.

Plants of the new *Chrysanthemum* differ primarily from plants of the female parent selection in the following characteristics:

1. Leaves of plants of the new *Chrysanthemum* have shallower proximal sinuses than leaves of plants of the female parent selection.
2. Inflorescences of plants of the new *Chrysanthemum* have more ray florets than inflorescences of plants of the female parent selection.

Plants of the new *Chrysanthemum* differ primarily from plants of the male parent selection in the following characteristics:

1. Disc florets of plants of the new *Chrysanthemum* are longer than disc florets of plants of the male parent selection.
2. Plants of the new *Chrysanthemum* are more resistant to White Rust than plants of the male parent selection.

Plants of the new *Chrysanthemum* can be compared to plants of *Chrysanthemum* X *morifolium* 'Annecy White', not patented. In side-by-side comparisons, plants of the new *Chrysanthemum* differ primarily from plants of 'Annecy White' in inflorescence size as plants of the new *Chrysanthemum* have smaller inflorescence than plants of 'Annecy White'.

BRIEF DESCRIPTION OF THE PHOTOGRAPHS

The accompanying photographs illustrate the overall appearance of the new *Chrysanthemum* plant showing the colors as true as it is reasonably possible to obtain in colored reproductions of this type.

The photograph on the first sheet (FIG. 1) is a side perspective view of a typical flowering stem of 'DLFMARA1' grown as a spray-type cut flower.

Figure 2:
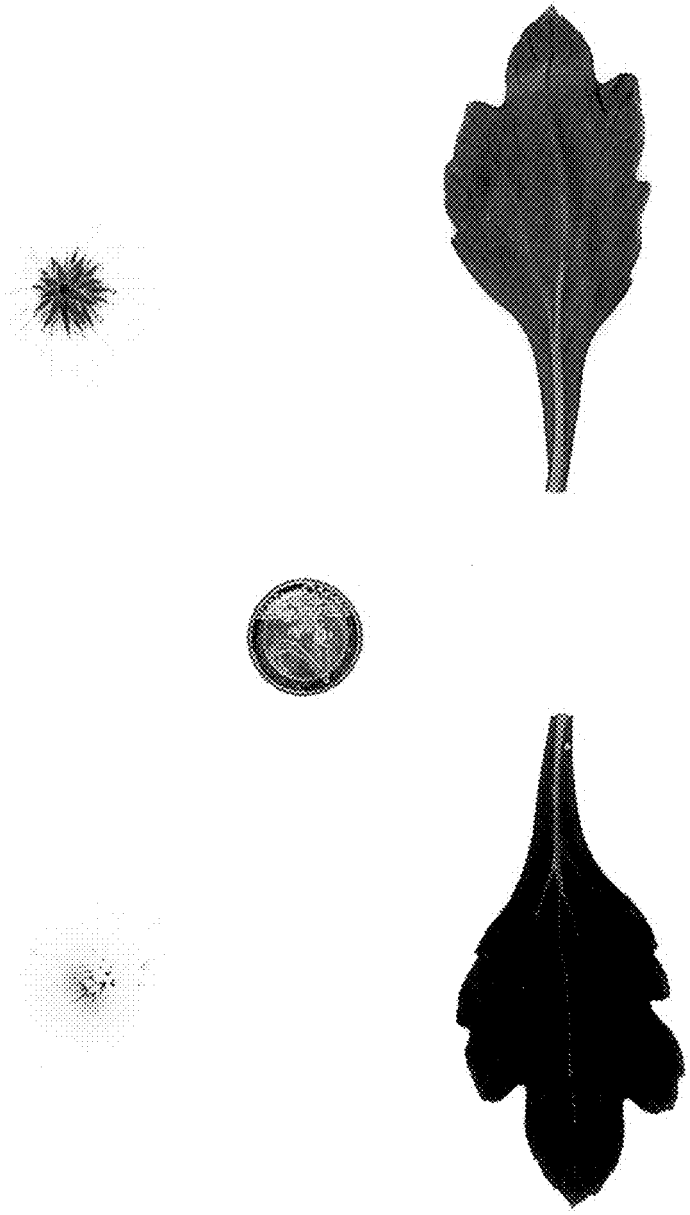

The photograph on the second sheet (FIG. 2) is a close-up view of upper (left) and lower (right) surfaces of typical inflorescences and typical leaves of 'DLFMARA1'.

DETAILED BOTANICAL DESCRIPTION

The aforementioned photographs and following observations and measurements describe plants grown during the autumn in ground beds in a glass-covered greenhouse in Maasdijk, The Netherlands and under cultural practices typical of commercial cut *Chrysanthemum* production. Plants were initially given long day/short night treatments followed by short day/long night treatments to induce flower initiation and development. During the production of the plants, day temperatures ranged from 18° C. to 25° C., night temperatures ranged from 20° C. to 22° C. and light levels averaged 8 klux. Plants were grown as single-stem spray-type plants and were eight weeks old when the photographs and the description were taken. In the following description, color references are made to The Royal Horticultural Society Colour Chart, 2015 Edition, except where general terms of ordinary dictionary significance are used.

Botanical classification: *Chrysanthemum* X *morifolium* 'DLFMARA1'.

Parentage:

*Female, or seed, parent*.—Proprietary selection of *Chrysanthemum* x *morifolium* identified as code number KR 2008.6601-1, not patented.

*Male, or pollen, parent*.—Proprietary selection of *Chrysanthemum* x *morifolium* identified as code number KR 2013.2342-1, not patented.

Propagation:

*Type*.—Terminal vegetative cuttings.

*Time to initiate roots, summer*.—About six days at temperatures about 24° C.

*Time to initiate roots, winter*.—About eight days at temperatures about 22° C.

*Time to produce a rooted young plant, summer*.—About twelve days at temperatures about 24° C.

*Time to produce a rooted young plant, winter*.—About two weeks at temperatures about 22° C.

*Root description*.—Fine, fibrous; typically creamy white in color, actual color of the roots is dependent on substrate composition, water quality, fertilizers, substrate temperature and physiological age of roots.

*Rooting habit*.—Freely branching, medium density.

Plant description:

*Plant and growth habit*.—Herbaceous anemone-type cut flower that is typically grown as a single stem spray-type; upright plant habit; vigorous growth habit and rapid growth rate.

*Plant height, soil level to top of foliar plane*.—About 68.9 cm.

*Plant height, soil level to top of inflorescence plane*.—About 73.8 cm.

*Plant (spray) diameter*.—About 16.9 cm.

*Flowering stem length*.—About 63.9 cm.

*Flowering stem diameter*.—About 6 mm.

*Flowering stem internode length*.—About 3 cm.

*Flowering stem strength*.—Strong.

*Flowering stem aspect*.—Erect.

*Flowering stem texture and luster*.—Moderately pubescent; slightly glossy.

*Flowering stem color, developing*.—Close to 137C.

*Flowering stem color, developed*.—Close to 143B to 143C; at the ridges, tinged with close to 177C to 177D.

*Leaf description*.—Arrangement: Alternate; simple. Length: About 10.3 cm. Width: About 4.9 cm. Shape, in overall outline: Obovate to broadly elliptic and oblong. Apex: Short apiculate. Base: Long attenuate. Margin: Palmately lobed, coarsely dentate to serrate; sinuses divergent and medium in depth. Texture and luster, upper surface: Moderately pubescent; not rugose; slightly velvety; matte to slightly glossy. Texture and luster, lower surface: Densely pubescent; not rugose; slightly velvety; slightly glossy. Venation pattern: Pinnate. Color: Developing leaves, upper surface: Close to 137B. Developing leaves, lower surface: Close to a blend of 146B and 147B. Fully developed leaves, upper surface: Close to NN137A; venation, close to 143B. Fully developed leaves, lower surface: Close to 147B; venation, close to 146B to 146C. Petioles: Length: About 5 mm. Diameter: About 2.5 mm by 4.5 mm. Strength: Moderately strong. Texture and luster, upper and lower surfaces: Moderately pubescent; moderately glossy. Color, upper surface: Close to 146B; edges, close to NN137B. Color, lower surface: Close to 146C; edges, close to 147B. Stipules: Quantity and appearance: Two leafy stipules, opposite, at the petiole attachment to the stem. Length: About 5 mm. Width: About 5 mm. Shape: Deltoid to broadly ovate; apex, apiculate to acute; base, broadly cuneate; margins, entire. Texture and luster, upper surface: Moderately pubescent; matte to slightly glossy. Texture and luster, lower surface: Densely pubescent; slightly glossy. Color, upper surface: Close to NN137A. Color, lower surface: Close to 147B.

Inflorescence description:

*Appearance*.—Anemone-type inflorescence form with tubular-shaped ray and disc florets; inflorescences, rotate and flattened globular in overall shape; inflorescences borne perpendicular to peduncles and face upright; ray and disc florets develop acropetally on a capitulum.

*Fragrance*.—Faintly fragrant; typical of *Chrysanthemums*.

*Flowering response*.—Under natural conditions, plant flower in the autumn/winter in the Northern Hemisphere; at other times of the year, inflorescence initiation and development can be induced under short day/long night conditions (at least 13.5 hours of darkness); uniform flowering habit and short response time, plants exposed to two weeks of long day/short night conditions after planting followed by photoinductive short day/long night conditions flower about 43 days later when grown as a spray-type.

*Postproduction longevity*.—Good postproduction longevity; after a seven-day storage period, cut flowers will maintain good color and substance for about two weeks in an interior environment; inflorescences persistent.

*Quantity of inflorescences*.—Only grown as a spray-type, typically about 15 to 27 inflorescences will develop per flowering stem.

*Inflorescence size*.—Diameter: About 5 cm. Depth (height): About 2.2 cm. Disc diameter: About 2.7 cm; conspicuous.

*Receptacles*.—Height: About 3.5 mm. Diameter: About 5 mm. Shape: Broadly deltoid. Color: Close to 145B.

*Inflorescence buds*.—Height: About 9 mm. Diameter: About 1.2 cm. Shape: Flattened globular. Texture and luster: Slightly to moderately pubescent; slightly glossy. Color: Developing involucral bracts, close to 137B and 145B; developing ray florets, close to 155C.

*Ray florets*.—Quantity and arrangement: About 29 to 34 arranged in a single whorl. Length: About 2.6 cm, varying between 2.4 cm and 2.8 cm. Width: About 3 mm. Shape: Tubular; margins fused, only open at the apex. Apex: Retuse to shallowly emarginate. Margin, free part: Entire. Aspect: About 60° from vertical. Texture and luster, inner surface: Smooth, glabrous; slightly velvety; matte. Texture and luster, outer surface: Smooth, glabrous; slightly velvety; slightly glossy. Color: When opening, inner and outer surfaces: Close to NN155D. Fully opened, inner and outer surfaces: Close to NN155D; towards the base, close to 145A; venation, similar to lamina colors; color does not change with subsequent development.

*Disc florets*.—Quantity and arrangement: About 200 spirally arranged at the center of the receptacle in about ten whorls. Length: About 1.5 cm. Diameter: About 2.5 mm. Shape: Tubular. Apex: Retuse to shallowly emarginate. Margin, free part: Entire. Texture and luster, inner surface: Smooth, glabrous; slightly velvety; matte. Texture and luster, outer surface: Smooth, glabrous; slightly velvety; slightly glossy. Color: When opening, inner and outer surfaces: Close to 145D; towards the apex, close to 150A. Fully opened, inner and outer surfaces: Close to NN155D; towards the base, close to 145A; color does not change with subsequent development.

*Involucral bracts*.—Quantity and arrangement: About 28 arranged in about three whorls. Length: About 1 cm. Width: About 2.5 mm. Shape: Oblong to narrowly ovate. Apex: Bluntly acute. Base: Cuneate. Margin: Entire. Texture and luster, upper surface: Smooth, glabrous; glossy. Texture and luster, lower surface: Moderately pubescent; matte. Color, upper surface: Close to 143A; lateral margins, translucent and close to 156D, apical margins tinged with close to 199C. Color, lower surface: Close to 137A; lateral margins, translucent and close to 156D, apical margins tinged with close to 199C.

*Peduncles*.—Length, terminal peduncle: About 7.6 cm. Diameter, terminal peduncle: About 2.5 mm. Length, third peduncle: About 7.9 cm. Diameter, third peduncle: About 2.5 mm. Strength, all peduncles: Strong. Aspect, terminal peduncle: Upright. Aspect, third peduncle: About 30° from vertical. Texture and luster, all peduncles: Moderately to densely pubescent; slightly glossy. Color, all peduncles: Close to 143A.

*Reproductive organs*.—Androecium: Present on disc florets only. Quantity: About five per floret. Filament length: About 2.5 mm. Filament color: Close to 145C. Anther size: About 2 mm by 5 mm. Anther shape: Narrowly oblong. Anther color: Close to 13A. Pollen amount: Scarce. Pollen color: Close to 13C to 13D. Gynoecium: Present on both ray and disc florets. Quantity: One per floret. Pistil length: About 5 mm. Style length: About 4 mm. Style color: Close to 150C. Stigma diameter: About 0.2 mm. Stigma shape: Cleft, decurrent. Stigma color: Close to 153D. Ovary color: Close to 157A.

*Seeds and fruits*.—To date, seed and fruit development have not been observed on plants of the new *Chrysanthemum*.

Pathogen & pest resistance: Plants of the new *Chrysanthemum* have been observed to be relatively resistant to White Rust PhNL1 (*Puccinia horiana*). To date, plants of the new *Chrysanthemum* have not been observed to be resistant to pest and other pathogens common to *Chrysanthemum* plants grown under commercial conditions.

Temperature tolerance: Plants of the new *Chrysanthemum* have been observed to tolerate temperatures ranging from about −12° C. to 35° C. and to be suitable for USDA Hardiness Zones 8 to 10.

It is claimed:

1. A new and distinct *Chrysanthemum* plant named 'DLFMARA1' as illustrated and described.

* * * * *